(12) United States Patent
Raman et al.

(10) Patent No.: US 10,745,693 B2
(45) Date of Patent: Aug. 18, 2020

(54) METHODS OF DESIGNING PROGRAMMABLE INDUCIBLE PROMOTERS

(71) Applicant: WISCONSIN ALUMNI RESEARCH FOUNDATION, Madison, WI (US)

(72) Inventors: Srivatsan Raman, Middleton, WI (US); Aseem Zoe Ansari, Madison, WI (US); Xiangyang Liu, Madison, WI (US); Jose Arcadio Rodriguez-Martinez, Dorado, PR (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 122 days.

(21) Appl. No.: 15/945,050

(22) Filed: Apr. 4, 2018

(65) Prior Publication Data
US 2019/0062730 A1    Feb. 28, 2019

Related U.S. Application Data

(60) Provisional application No. 62/481,426, filed on Apr. 4, 2017.

(51) Int. Cl.
*C12N 15/10* (2006.01)

(52) U.S. Cl.
CPC ..... *C12N 15/1065* (2013.01); *C12N 15/1051* (2013.01); *C12N 15/1058* (2013.01); *C12N 15/1086* (2013.01)

(58) Field of Classification Search
CPC .................................................. C12N 15/1065
USPC ............................................................ 506/2
See application file for complete search history.

(56) References Cited

U.S. PATENT DOCUMENTS

| 6,537,779 B1 | 3/2003 | Kara et al. |
| 8,652,804 B2 | 2/2014 | Dietrich et al. |
| 2005/0227246 A1* | 10/2005 | Hahm ................ C12N 15/1086 435/6.13 |
| 2010/0159457 A1 | 6/2010 | Warren et al. |

FOREIGN PATENT DOCUMENTS

EP         2668277 B1    11/2016

* cited by examiner

*Primary Examiner* — Karla A Dines
(74) *Attorney, Agent, or Firm* — Cantor Colburn LLP

(57) ABSTRACT

Described herein is a method for identifying synthetic inducible promoters that have specified induction and/or repression for DNA binding proteins such as an allosteric transcription factor and an inducer molecule. The method includes an in vitro selection from an unselected polynucleotide library comprising a plurality of random degeneracies, and an in vivo selection to produce an induced promoter library. Produced is an induction table, which allows the selection of a promoter with specific induction and/or repression properties. Also included are biosensors containing the synthetic inducible promoters.

17 Claims, 7 Drawing Sheets
(7 of 7 Drawing Sheet(s) Filed in Color)
Specification includes a Sequence Listing.

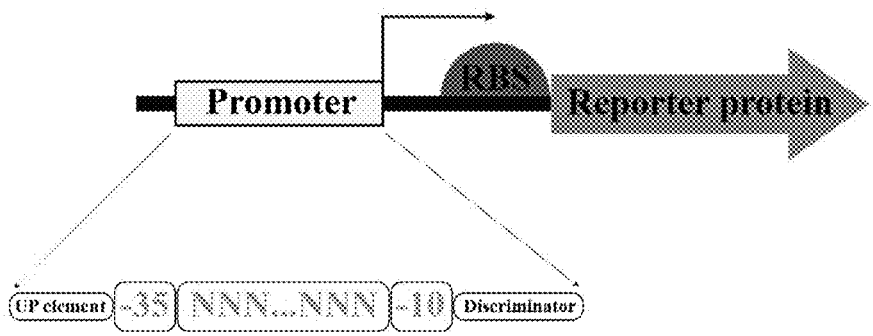

CSI Control Library-BsaI (SEQ ID NO: 2):
TGCGACGGTCTCACTGAGGCGCGCCTTGACATCGCATCTTTTTGTACCTATAATAGAT-
TCATGATGAGAATTCATTAAAGAGGAGAAAGGT
CSI 16N-BsaI (SEQ ID NO: 3):
TGCGACGGTCTCACTGAGGCGCGCCTTGACANNNNNNNNNNNNNNNNTATAATAGATTCAT-
GATGAGAATTCATTAAAGAGGAGAAAGGT
CSI 17N-BsaI (SEQ ID NO: 4):
TGCGACGGTCTCACTGAGGCGCGCCTTGACANNNNNNNNNNNNNNNNNTATAATAGAT-
TCATGATGAGAATTCATTAAAGAGGAGAAAGGT
CSI 18N-BsaI (SEQ ID NO: 5):
TGCGACGGTCTCACTGAGGCGCGCCTTGACANNNNNNNNNNNNNNNNNNTATAATAGAT-
TCATGATGAGAATTCATTAAAGAGGAGAAAGGT
CSI 19N-BsaI (SEQ ID NO: 6):
TGCGACGGTCTCACTGAGGCGCGCCTTGACANNNNNNNNNNNNNNNNNNNTATAATAGAT-
TCATGATGAGAATTCATTAAAGAGGAGAAAGGT Color scheme:
BsaI recognition site
BsaI cut site
-35 and -10 sites
RBS
Control spacer
Degenerated spacer library

FIG. 4

SEQUENCE LISTING

<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Ribosome binding site

<400> SEQUENCE: 1
gaattcatta aagaggagaa aggt                                              24

<210> SEQ ID NO 2
<211> LENGTH: 91
<212> TYPE: DNA
<213> ORGANISM: Artificial
<220> FEATURE:
<223> OTHER INFORMATION: Control Sequence

<400> SEQUENCE: 2
tgcgacggtc tcactgaggc gcgccttgac atcgcatctt tttgtaccta taatagattc       60
atgatgagaa ttcattaaag aggagaaagg t                                      91

<210> SEQ ID NO 3
<211> LENGTH: 90
<212> TYPE: DNA
<213> ORGANISM: Artificial
<220> FEATURE:
<223> OTHER INFORMATION: CSI 16N-BsaI
<220> FEATURE:
<221> NAME/KEY: misc_feature
<222> LOCATION: (32)..(47)
<223> OTHER INFORMATION: n is a, c, g, or t

<400> SEQUENCE: 3
tgcgacggtc tcactgaggc gcgccttgac annnnnnnnn nnnnnnntat aatagattca       60
tgatgagaat tcattaaaga ggagaaaggt                                        90

<210> SEQ ID NO 4
<211> LENGTH: 91
<212> TYPE: DNA
<213> ORGANISM: Artificial
<220> FEATURE:
<223> OTHER INFORMATION: CSI 17N-BsaI
<220> FEATURE:
<221> NAME/KEY: misc_feature
<222> LOCATION: (32)..(48)
<223> OTHER INFORMATION: n is a, c, g, or t

<400> SEQUENCE: 4
tgcgacggtc tcactgaggc gcgccttgac annnnnnnnn nnnnnnnta taatagattc        60 atgatgagaa ttcattaaag aggagaaagg t                                      91

<210> SEQ ID NO 5
<211> LENGTH: 92
<212> TYPE: DNA
<213> ORGANISM: Artificial
<220> FEATURE:
<223> OTHER INFORMATION: CSI 18N-BsaI
<220> FEATURE:
<221> NAME/KEY: misc_feature
<222> LOCATION: (32)..(49)
<223> OTHER INFORMATION: n is a, c, g, or t

<400> SEQUENCE: 5
tgcgacggtc tcactgaggc gcgccttgac annnnnnnnn nnnnnnnnt ataatagatt        60 catgatgaga attcattaaa gaggagaaag gt                                        92

<210> SEQ ID NO 6
<211> LENGTH: 93
<212> TYPE: DNA
<213> ORGANISM: Artificial
<220> FEATURE:
<223> OTHER INFORMATION: CSI 19N-BsaI
<220> FEATURE:
<221> NAME/KEY: misc_feature
<222> LOCATION: (32)..(50)
<223> OTHER INFORMATION: n is a, c, g, or t

<400> SEQUENCE: 6
tgcgacggtc tcactgaggc gcgccttgac annnnnnnnn nnnnnnnnnn tataatagat         60
tcatgatgag aattcattaa agaggagaaa ggt                                       93

<210> SEQ ID NO 7
<211> LENGTH: 30
<212> TYPE: DNA
<213> ORGANISM: Artificial
<220> FEATURE:
<223> OTHER INFORMATION: promoter sequence

<400> SEQUENCE: 7
ttgacataca tacgcgtgtg tatgtataat                                           30

<210> SEQ ID NO 8
<211> LENGTH: 28
<212> TYPE: DNA
<213> ORGANISM: Artificial
<220> FEATURE:
<223> OTHER INFORMATION: promoter sequence

<400> SEQUENCE: 8
ttgacataca atcacggttg tatataat                                             28

<210> SEQ ID NO 9
<211> LENGTH: 31
<212> TYPE: DNA
<213> ORGANISM: Artificial
<220> FEATURE:
<223> OTHER INFORMATION: promoter sequence

<400> SEQUENCE: 9
ttgacataca tgcgtgaatg tatgttataa t                                         31

<210> SEQ ID NO 10
<211> LENGTH: 30
<212> TYPE: DNA
<213> ORGANISM: Artificial
<220> FEATURE:
<223> OTHER INFORMATION: promoter sequence

<400> SEQUENCE: 10
ttgacataca tccatgagtg tatgtataat                                           30

<210> SEQ ID NO 11
<211> LENGTH: 39
<212> TYPE: DNA
<213> ORGANISM: Artificial
<220> FEATURE:
<223> OTHER INFORMATION: promoter sequence

<400> SEQUENCE: 11

```
gtttacaaac aaccgcgaat gtaagtatat tccttagca                              39

<210> SEQ ID NO 12
<211> LENGTH: 40
<212> TYPE: DNA
<213> ORGANISM: Artificial
<220> FEATURE:
<223> OTHER INFORMATION: promoter sequence

<400> SEQUENCE: 12
tatttacaaa caaccatgaa tgtaagtata ttccttagca                             40

<210> SEQ ID NO 13
<211> LENGTH: 38
<212> TYPE: DNA
<213> ORGANISM: Artificial
<220> FEATURE:
<223> OTHER INFORMATION: promoter sequence

<400> SEQUENCE: 13
ttgacgctgg tcatttaaga actgtatcgt acagtact                               38

<210> SEQ ID NO 14
<211> LENGTH: 39
<212> TYPE: DNA
<213> ORGANISM: Artificial
<220> FEATURE:
<223> OTHER INFORMATION: promoter sequence

<400> SEQUENCE: 14
tttctgtaat aaatattaca atttttaatt taattttttc                             39

<210> SEQ ID NO 15
<211> LENGTH: 41
<212> TYPE: DNA
<213> ORGANISM: Artificial
<220> FEATURE:
<223> OTHER INFORMATION: promoter sequence

<400> SEQUENCE: 15
tttacaaaca aacaagcatg tatgtatatt tcgcacccat c                           41

<210> SEQ ID NO 16
<211> LENGTH: 60
<212> TYPE: DNA
<213> ORGANISM: Artificial
<220> FEATURE:
<223> OTHER INFORMATION: promoter sequence

<400> SEQUENCE: 16
agtgaacgct tgttgactcg attgcgcgga acgggcaaag ttttgtgaac gatcgttcac       60
```

METHODS OF DESIGNING PROGRAMMABLE INDUCIBLE PROMOTERS

CROSS-REFERENCE TO RELATED APPLICATIONS

This application claims priority to U.S. Provisional Application 62/481,426 filed on Apr. 4, 2017, which is incorporated herein by reference in its entirety.

STATEMENT REGARDING FEDERALLY SPONSORED RESEARCH & DEVELOPMENT

This invention was made with government support under DE-FC02-07ER64494 awarded by the US Department of Energy. The government has certain rights in the invention.

FIELD OF THE DISCLOSURE

The present disclosure is related to de novo methods for designing synthetic inducible promoters and the use of the promoters in, for example, biosensor applications.

BACKGROUND

Biosensors to detect small molecule ligands (e.g., metabolites) have applications in synthetic biology, medical diagnosis, environmental monitoring, bioremediation, and bioenergy. Protein-based biosensors are autonomous, self-powered, miniaturizable, and programmable macromolecules that function in both in vivo and ex vivo environments. Allosteric transcription factors (aTFs), a family of regulatory proteins found in all kingdoms of life, are widely used as biosensors in synthetic biology. Bacterial aTFs, such as LacI or TetR, are composed of allosterically-linked ligand- and DNA-binding domains. When an aTF binds to a ligand, the protein undergoes a conformational change, causing a change in affinity for DNA. In the case of transcription repressors, the loss of DNA affinity allows the RNA polymerase to access the promoter and initiate transcription of the downstream gene. Therefore, the concentration of small molecule can be measured in terms of a reporter gene expression in a dose-dependent manner.

Natural aTF-promoter pairs, however, may be unsuitable for a wide-range of biosensor applications. What is needed are methods of designing synthetic promoters for aTFs that can provide desired induction properties for aTF-based biosensors.

BRIEF SUMMARY

In an aspect, a method of identifying a synthetic inducible promoter, comprises
in vitro selecting a first population of polynucleotides that bind to a DNA binding protein to produce an enriched polynucleotide library by
providing an unselected polynucleotide library comprising a plurality of random degeneracies over one or more regions of a 12 to 40 base pair polynucleotide sequence, and
selecting from the unselected polynucleotide library a plurality of polynucleotide sequences that bind the DNA binding protein to provide the enriched polynucleotide library;
in vivo selecting from the enriched polynucleotide library a second population of polynucleotides that repress or induce production of a reporter protein to produce an induced promoter library by
operably linking the enriched polynucleotide library to a ribosome binding site and a reporter gene to provide a plurality of reporter vectors,
transforming the plurality of reporter vectors into a host strain which co-expresses the DNA binding protein, and growing the host strain provide a culture, and
dividing the culture into two split cultures and adding an inducer molecule for the DNA binding protein into one of the two split cultures to provide a non-induced culture and an induced culture, and
sorting a control culture transformed with the plurality of reporter vectors with no DNA binding protein expression, the non-induced culture, and the induced culture by reporter protein intensity, to provide a sorted control culture, a sorted non-induced culture, and a sorted induced culture, and
binning the sorted control culture, the sorted non-induced culture and the sorted induced culture to produce one or more control gates, one or more non-induced gates and one or more induced gates, wherein the one or more control gates comprises a control promoter library, the one or more non-induced gates comprises a non-induced promoter library, and the one or more induced gates comprises the induced promoter library, wherein a gate is a culture portion comprising a plurality of promoters of specified reporter intensities;
sequencing and analyzing the control promoter library, the non-induced promoter library and the induced promoter library by
culturing and then amplifying the control promoter library, the non-induced promoter library and the induced promoter library, to provide an amplified control promoter library, an amplified non-induced promoter library and an amplified induced promoter library,
quantitatively next generation sequencing the amplified control promoter library, the amplified non-induced promoter library, and the amplified induced promoter library to provide a plurality of sequenced promoters,
providing a control metric, a non-induced metric, and/or an induced metric for at least a portion of the plurality of sequenced promoters based upon identification of each of the at least a portion of the plurality of sequenced promoters in the control promoter library, the non-induced promoter library and/or the induced promoter library,
determining, from the control metric, the non-induced metric and the induced metric for each of the at least a portion of the plurality of sequenced promoters an induction/repression property, and
providing an induction table including each of the at least a portion of the plurality of sequenced promoters comprising the promoter sequence and the control metric, non-induced metric, and induced metric, wherein the control metric, non-induced metric, and induced metric provide an induction/repression property of the promoter sequence for the DNA binding protein and the inducer molecule;
and
selecting, based upon the induction table, a synthetic promoter having a specified induction and/or repression for the DNA binding protein and the inducer molecule.

In another aspect, also included herein is a biosensor comprising a synthetic promoter identified by the foregoing process, wherein the biosensor is responsive to the concentration of the inducer molecule.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 shows an exemplary library design.

The above-described and other features will be appreciated and understood by those skilled in the art from the following detailed description, drawings, and appended claims.

DETAILED DESCRIPTION

The inventors of the present application recognized that known aTF-promoter pairs suffer from several limitations. An aTF from one host may not work in a heterologous host due to, for example, promoter incompatibility and the presence of cryptic internal regulatory sequences. The dynamic range of a natural promoter may be unsuitable for biosensor applications. In addition, the DNA binding sequence of many natural aTFs is unknown. These shortcomings restrict the wide applicability and portability of aTF biosensors.

Figure 1:
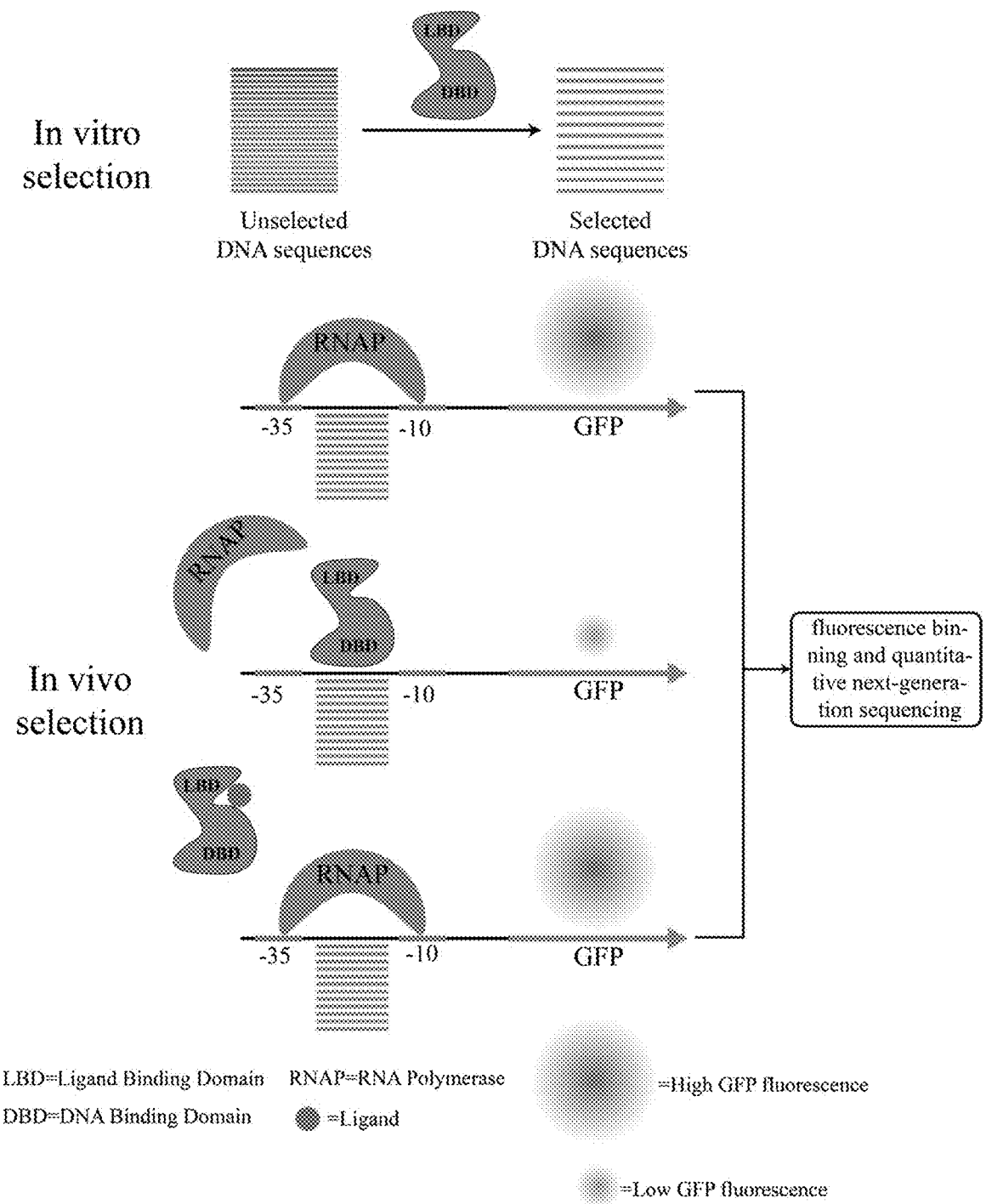
FIG. 1 is a schematic of the overall method to produce synthetic inducible promoters.

The inventors have developed a method for de novo design of synthetic inducible promoters for transcription factors and other DNA binding proteins such as aTFs with tunable dynamic range behavior, and compatibility with virtually any host organism. The method can include selecting inducible promoters, for example, by converting a constitutive promoter of an organism into an inducible promoter by introducing binding sites near the RNA polymerase binding site. By controlling the access of a transcription factor and the RNA polymerase to the promoter, the dynamic range of the system can be controlled. Briefly, the method includes three steps: first, in vitro selection is used to identify tens of thousands of DNA sequences with varying affinities to the transcription factor or other DNA binding protein; second, in vivo transcription of a fluorescent reporter is driven by synthetic promoters containing these in vitro selected transcription factor or other DNA binding protein DNA binding sequences to provide a population of polynucleotides that repress or induce production of the reporter protein; and third, the induction properties of the promoters (tens of thousands) are simultaneously characterized by fluorescence binning and quantitative next-generation sequencing to enable selection of synthetic promoters having a specified induction and/or repression for the transcription factor or other DNA binding protein and the inducer molecule. An embodiment of the method is provided in FIG. 1.

In an embodiment, the method can provide novel promoters of known transcription factors and other DNA binding proteins. Such novel promoters allow for reengineering well-characterized transcription factors and other DNA binding proteins. In another embodiment, the method can provide promoters for natural transcription factors and other DNA binding proteins in the database which do not have known promoters. The method provides for tunable transcription factor-promoter pairs and DNA binding protein-promoter pairs for biosensor applications.

A method of identifying a synthetic inducible promoter, comprises
  in vitro selecting a first population of polynucleotides that bind to a DNA binding protein to produce an enriched polynucleotide library by
    providing an unselected polynucleotide library comprising a plurality of random degeneracies over one or more regions of a 12 to 40 base pair polynucleotide sequence, and
    selecting from the unselected polynucleotide library a plurality of polynucleotide sequences that bind the DNA binding protein to provide the enriched polynucleotide library;
  in vivo selecting from the enriched polynucleotide library a second population of polynucleotides that repress or induce production of a reporter protein to produce an induced polynucleotide library by
    operably linking the enriched polynucleotide library to a ribosome binding site and a reporter gene to provide a plurality of reporter vectors,
    transforming the plurality of reporter vectors into a host strain which co-expresses the DNA binding protein, and growing the host strain provide a culture, and
    dividing the culture into two split cultures and adding an inducer molecule for the DNA binding protein into one of the two split cultures to provide a non-induced culture and an induced culture, and
    sorting a control culture transformed with the plurality of reporter vectors with no DNA binding protein expression, the non-induced culture, and the induced culture by reporter protein intensity, to provide a sorted control culture, a sorted non-induced culture, and a sorted induced culture, and
    binning the sorted control culture, the sorted non-induced culture and the sorted induced culture to produce one or more control gates, one or more non-induced gates and one or more induced gates, wherein the one or more control gates comprises a control promoter library, the one or more non-induced gates comprises a non-induced promoter library, and the one or more induced gates comprises the induced promoter library, wherein a gate is a culture portion comprising a plurality of promoters of specified reporter intensities;
  sequencing and analyzing the control promoter library, the non-induced promoter library and the induced promoter library by
    culturing and then amplifying the control promoter library, the non-induced promoter library and the induced promoter library, to provide an amplified control promoter library, an amplified non-induced promoter library and an amplified induced promoter library, quantitatively next generation sequencing the amplified control promoter library, the amplified non-induced promoter library, and the amplified induced promoter library to provide a plurality of sequenced promoters, providing a control metric, a non-induced metric, and/or an induced metric for at least a portion of the plurality of sequenced promoters based upon identification of each of the at least a portion of the plurality of sequenced promoters in the control promoter library, the non-induced promoter library and/or the induced promoter library, determining, from the control metric, the non-induced metric and the induced metric for each of the at least a portion of the plurality of sequenced promoters an induction/repression property, and providing an induction table including each of the at least a portion of the plurality of sequenced promoters comprising the promoter sequence and the control metric, non-induced metric, and induced metric, wherein the control metric, non-induced metric, and induced metric provide an induction/repression property of the promoter sequence for the DNA binding protein and the inducer molecule; and selecting, based upon the induction table, a synthetic promoter having a specified induction and/or repression for the DNA binding protein and the inducer molecule.

In an embodiment, the DNA binding protein is an allosteric transcription factor such as a bacterial transcription factor. In other embodiments, the DNA binding protein is an allosteric activator, a two-component signaling protein, or a eukaryotic nuclear receptor.

In an embodiment, the steps in the method can be performed in a different order. For example, the sequencing step can be performed after the in vitro selection. In this embodiment, one can identify the highly enriched sequences and clone them for the in vivo step. Alternatively, one can start with the in vivo step and identify functional promoters with high activity. These high activity sequences can then be used in the in vitro step to identify promoters with high affinity to DNA binding proteins. One can then follow up with binning and sorting to identify genotypes and phenotypes.

Exemplary DNA binding proteins include bacterial transcription factor (repressor): TetR, LacI, TtgR, MphR; bacterial transcription factor (activator): AraC, LysR; two-component signaling proteins: PhoP/PhoQ, EnvZ/OmpR, KdpE/KdpD; eukaryotic nuclear receptor: glucocorticoid receptor, mineralocorticoid receptor, estrogen receptor, and others. Table 1 provides exemplary transcription factors.

TABLE 1

| Exemplary transcription factors | | |
|---|---|---|
| System | Transcription factor family | Example transcription factors |
| Prokaryotes-One component | LTTR | LysR, AtzR, AlsR, ArgP, BenM, CidR, CynR, HvrB, ToxR, OccR, NodD, NocR, NahR IlvY, MetR, MdcR, CysB |
| | AraC/XylS | AraC, XylS, RhaR, RhaS, UreR, Rob, Rns, MelR |
| | DeoR | DeoR, GlpR, GutR, FucR, UlaR, LacR, FruR, IolR, AccR |
| | DtxR | DtxR, SloR, MtsR, MntR |

TABLE 1-continued

| Exemplary transcription factors | | |
|---|---|---|
| System | Transcription factor family | Example transcription factors |
| | Fur | Fur, Zur, Mur, Nur |
| | GntR | GntR, FadR, HutC, MocR, YtrA, AraR, DevA, PlmA |
| | LuxR | LuxR, AhyR, QscR, HapR |
| | Lrp/AsnC | Lrp, AsnC, LrpA, LrpC |
| | Crp/Fnr | Crp, FnR, Vfr, |
| | IclR | IclR, RexZ, SsfR, |
| | MerR | MerR, BltR, BmrR, Mta, CueR, ZntR, PbrR |
| | MarR | MarR, OhrR, SlyA, MosR, RovA, MepR |
| | LacI/GalR | LacI, CcpA, GalR, PurR, CytR, CRA |
| | Amino acid metabolism | ArgR, Trp |
| | TetR | TetR, AcuR, AguR, BepR, CmeR, ComR, CymR, DesT, EthR, FabR, FrrA, HdnoR, HrtR, LanK, LrfR, LmrA, NalC, MphR, PaaR, Pip, QacR, RolR, SimR, SmeT, TtgR, VarR, VceR |
| Prokaryotes-two component | | PhoP/PhoQ, EnvZ/OmpR, KdpE/KdpD, ComA/ComP |
| Eukaryotes | Nuclear receptor | NR3C1, NR3A1, NR3C2 |

Exemplary allosteric activators include LysR, AtzR, IlvY, MetR, MdcR, CysB, AraC, XylS, RhaR, UreR, LuxR, AhyR, QscR, HapR, Lrp, AsnC, LrpA, LrpC, Crp, FnR, Vfr, IclR, RexZ, SsfR, MerR, BltR, BmrR, Mta, CueR, ZntR, PbrR, and DhaS.

Inducers include a sugar molecule, a metallic ion, an antimicrobial agent, a dye, a flavonoid, or a combination comprising at least one of the foregoing. Specific inducers include taurocholate, a cholate, a salicylate, p-cumate, p-cymene, a stearate, a flavonoid, a chlorinated phenol, an alkaloid, resorcinol, triclosan, tetracycline, phloretin, naringenin, or quercetin. Table 2 provides exemplary inducers.

TABLE 2

| Exemplary inducers | |
|---|---|
| Types of molecules | Example molecules |
| Sugar molecules | lactose, IPTG, L-arabinose, maltose, trehalose, glucose-6P, glycerol-P, glucitol, fucose, L-ascorbate, deoxyribonucleoside, inositol, fructose |
| Metallic ions | Hg(II), Cu(II), Ag(I), Au(I), Zn(II), Pb(II), Cd(II) |
| Antimicrobial agents | anhydrotetracyclin, chloramphenicol, resorcinol, proflavine, rifamycin, actinorhodin, simocyclinone D8, triclosan, |
| Dyes | ethidium, rhodamine6G, tetraphenylphosponim |
| Flavonoids | quercetin, fisetin, galangin, phlorotin, naringenin, cetachin, coumestrol |
| Non-sugar metabolites | stearate, Oleate, c-d-AMP, cholate, salicylate |
| Steroid hormones | glucocorticoid, estrogen mineralocorticoid |

The first step in the method is an in vitro selection in which a first population of polynucleotides that bind to a DNA binding protein is selected to produce an enriched polynucleotide library. The in vitro selection is done by first providing an unselected polynucleotide library comprising a plurality of random degeneracies over one or more regions of a 12 to 40 base pair polynucleotide sequence. In an aspect, the random degeneracies are over a 16 to 19 base pair sequence, see for example FIG. 4. The unselected polynucleotide library can be based upon a known constitutive promoter. Alternatively, the unselected polynucleotide library comprises any set of random degeneracies, for example, to identify operator sequences for a DNA binding protein of unknown specificity.

If the DNA binding protein binds as a dimer, the length of the polynucleotide can be varied to select for one dimer or multiple sequential dimers with user-defined spacing.

A plurality of polynucleotide sequences that bind the DNA binding protein are then selected from the unselected polynucleotide library to provide the enriched promoter library. The enriched polynucleotide library is enriched for sequences that bind the DNA binding protein factor with a range of affinities that can be determined by the experimenter, for example, by varying the buffer conditions used for binding, such as salt concentration and pH. For example, using low salt conditions may allow for a wide range of binding affinities, while high salt conditions will generally select higher affinity sequences. The enriched polynucleotide library thus includes a plurality of operator sequences that bind to the DNA binding protein with a range of affinities from sub-nanomolar to micromolar.

The in vitro selection can be performed by any suitable method such as a pull-down method, an electrophoretic mobility shift assay (EMSA) method, protein-binding microarrays, or other similar methods. In general, the DNA binding protein, the unselected polynucleotide library, or both may comprise a label such as an affinity tag, a radioactive tag or a fluorescent tag.

In an example of a pull-down method, the DNA binding protein is labeled with an affinity tag. Exemplary affinity tags include green fluorescent protein (GFP), glutathione-S-transferase (GST) and the FLAG®-peptide tag consisting of eight amino acids (AspTyrLysAspAspAspAspLys) including an enterokinase-cleavage site. The unselected polynucleotide library is incubated with the labeled DNA binding protein under selected buffer conditions that allow for binding of the allosteric transcription factor to selected polynucleotide sequences. Exemplary buffer conditions (PBS (Phosphate-buffered saline) pH 7.5, TBS(Tris-buffered saline) pH 7.5, HBS(HEPES-buffered saline) pH 7.5, or buffers optimized for individual proteins. Additional components for the buffer mix include poly dI-dC, BSA (bovine serum albumin), non-ionic detergent, reducing agent, a protease inhibitor cocktail, and the like. Magnetic beads, for example, can be used to pull down affinity labeled protein-DNA complexes, separating them from the unbound DNA sequences. The bound DNA sequences are amplified using PCR, for example, so that another round of selection may be performed. In an aspect, 3-5 rounds of in vitro selection are performed.

In another aspect, an EMSA method is used to select the enriched polynucleotide library. Either purified DNA binding protein or a cell lysate containing the DNA binding protein may be employed. Optionally, the binding specificity of the DNA binding protein factor is confirmed using the known genomic binding sequence (e.g., the same length DNA as the library) and an inducer for the DNA binding protein. The unselected polynucleotide library can be labeled with a radioactive or fluorescent label. The unselected polynucleotide library and the allosteric transcription factor are incubated under selected buffer conditions that allow for binding of the DNA binding protein to selected polynucleotide sequences. The binding mixture and a control are loaded on the same gel. The polynucleotide library sequences are cut from the gel at the same position as the bound genomic sequence. The DNA sequences are eluted from the gel, and magnetic beads, for example, are used to collect the DNA molecules. After amplification of the bound DNA sequences, one or more additional rounds of selection may be performed.

For a given DNA binding protein, the number of unique sequences found post in vitro enrichment depends on several factors including the existence of potential operator sequences in the random pool, expression of the DNA binding protein in the host cell, idiosyncratic DNA binding domain conformation, and potential toxicity of DNA binding protein expression.

The enriched polynucleotide library is a library of operator sequences for the DNA binding protein that bind the DNA binding protein with a range of affinities. The enriched library size can range from a few hundred to tens of thousands of operator sequences depending on the stringency of the selection. The higher the round of enrichment is, the lower the effective promoter diversity will be, however, the benefit is to obtain sequences with higher level of binding affinity.

Once the enriched polynucleotide library that is enriched for sequences that bind the DNA binding protein has been produced, the gene expression activity of the enriched polynucleotide library is measured in vivo to simultaneously compute the induction level of the members of the enriched polynucleotide library. The method thus includes in vivo selecting from the enriched polynucleotide library a second population of polynucleotides that repress or induce production of a reporter protein to produce an induced polynucleotide library.

The in vivo selection is carried out by first operably linking the enriched polynucleotide library to a constant ribosome binding site and a reporter gene to provide a plurality of reporter vectors. "Operably linked" means that the nucleotide sequence of interest is linked to the regulatory sequence(s) in a manner that allows for expression of the reporter gene. The enriched polynucleotide library can be operably linked in any location, or multiplicity, so long as it operably linked to allow for expression of the reporter gene.

Exemplary reporter proteins include GFP and FbFP(anaerobic condition).

In an aspect, the DNAs from the first enriched polynucleotide library are inserted into a constitutive promoter either between or flanking the RNA polymerase binding sites (e.g., containing the consensus −35 (TTGACA) and −10 sites (TATAAT) in the case of E. coli). This unit is operably linked to a ribosome binding site and a reporter gene (e.g., GFP), for example in an appropriate vector such as a plasmid, to produce a reporter vector. The enriched polynucleotide library can be operably linked to a transcription regulatory site, such as A TATA box. For example, the enriched polynucleotide library can be in the general vicinity of transcription regulatory sites such as TATA box in eukaryotes.

In an aspect, the polynucleotide library can be inserted at different locations on a promoter, as for example downstream of the −10 site, upstream of −35 site or overlapping these sites.

In an aspect, multiple polynucleotide libraries can be inserted along a promoter, that is, multiple polynucleotide libraries can be operably linked to the ribosome binding site and the reporter gene.

The plurality of reporter vectors is then transformed into a host strain which co-expresses the allosteric transcription factor, and the host strain is grown provide a culture.

Exemplary host can include both prokaryotes and eukaryotes. In an embodiment, the host strain comprises organisms of the genus *Escherichia, Bacillus, Staphylococcus, Cau-* lobacter, Streptococcus, Streptomyces, Mycoplasma, Aliivibrio, Synechocystis, Azotobacter, Pseudomonas, Agrobacterium, Zymomonas, Saccharomyces, Yarrowia, Pichia or a combination comprising at least one of the foregoing. Host strains and examples are provided in Table 3:

TABLE 3

Organism genera and example species

| System | Organism genus | Example species |
| --- | --- | --- |
| Prokaryotes | Escherichia | E. coli |
| | Bacillus | B. subtilis, B. thermophiles, B. anthracis |
| | Staphylococcus | S. aureus, S. epidermidis |
| | Caulobacter | C. Crescentus |
| | Streptococcus | S. pyogenes, S. pneumoniae |
| | Thermus | T. aquaticus, T. thermophilus |
| | Streptomyces | S. coelicolor, S. antibioticus, S. avermitilis |
| | Mycoplasma | M. Pneumoniae, M. genitalium |
| | Aliivibrio | A. fischeri |
| | Synechocystis | S. sp PCC6803 |
| | Azotobacter | A. vinelandii |
| | Pseudomonas | P. aeruginosa, P. putida, P. syringae |
| | Agrobacterium | A. tumefaciens |
| | Zymomonas | Z. mobills |
| Eukaryotes | Saccharomyces | S. cerevisiae |
| | Yarrowia | Y. lipolytica |
| | Pichia | P. pastoris |

Once the host strain culture has been grown, the culture is divided into two split cultures, and an inducer molecule for the DNA binding protein is added into one of the two split cultures to provide a non-induced culture and an induced culture. Exemplary aTF-inducer pairs are provided in Table 4.

TABLE 4

Exemplary aTF-inducer pairs

| | Inducer | Native host |
| --- | --- | --- |
| CmeR | Taurocholate, chelate, salicylate | Campylobacter jejuni |
| CymR | p-cumate, p-cymene | Pseudomonas putida |
| DesT | stearate | Pseudomonas aeruginosa |
| LmrA | flavonoids | Bacillus subtilis |
| NalC | chlorinated phenols | Pseudomonas aeruginosa |
| PmeR | flavonoids | Pseudomonas syringae |
| QacR | berberine (alkaloid) | Staphylococcus aureus |
| RolR | resorcinol | Corynebacterium glutamicum |
| SmeT | triclosan | Stenotrophomonas maltophilia |
| TetR | tetracycline | Escherichia coli |
| TtgR | phloretin, naringenin, quercetin | Pseudomonas putida |

A control culture is produced that is a culture transformed with the plurality of reporter vectors with no DNA binding protein expression.

The control culture, the non-induced culture and the induced culture are sorted by reporter protein intensity (e.g., fluorescence intensity), to provide a sorted control culture, a sorted non-induced culture, and a sorted induced culture. Sorting can be done, for example, using florescent-activated-cell-sorting (FACS), for example. FACS allows the separation of the target cell population from the rest of the population based on a given parameter (e.g., fluorescence). To separate the desired population, users can directly circle out the desired population (referred as "drawing gates" or "gating") on the population distribution graph in the corresponding program. Then the cell sorter executes the sorting based on the gates drawn.

Binning is then done to provide culture portions comprising a plurality of promoters that provide specified reporter intensities, referred to as gates. The gates provide a convenient means by which to group the control promoter sequences, non-induced promoter sequences and induced promoter sequences by activity level. The method thus includes binning the sorted control culture, the sorted non-induced culture and the sorted induced culture to produce one or more control gates, one or more non-induced gates and one or more induced gates, wherein the one or more control gates comprises a control promoter library, the one or more non-induced gates comprises a non-induced promoter library, and the one or more induced gates comprises the induced promoter library.

For example, the activity of each promoter sequence (enriched polynucleotide library member operably linked to a ribosome binding site) is measured in terms of reporter level, e.g., GFP level. To simultaneously measure the activity of all the promoter sequences, we classify them into bins based on GFP fluorescence. The number of bins is adjusted depending on the range of promoter activities exhibited. For instance, promoter activities over a 100 fold range are captured in 4-5 bins. The width of each bin is limited by the accuracy of cell sorting. A "gate" is applied in the cell sorter to collect cells within a specified fluorescence range. The gates provide a convenient means by which to group the control sequences, non-induced sequences and induced sequences by activity level. A gate is a portion of a culture comprising a plurality of promoters of specified reporter intensities. Cells containing the enriched polynucleotide library, enriched polynucleotide library+DNA binding protein, enriched polynucleotide library+DNA binding protein+inducer are thus sorted based on their activity.

The control promoter library, the non-induced promoter library, and the induced promoter library are then sequenced and analyzed. The control promoter library, the non-induced promoter library and the induced promoter library are cultured and amplified to provide an amplified control promoter library, an amplified non-induced promoter library and an amplified induced promoter library. Culturing is done, for example, overnight. Amplification can be done with a sequencing primer and a barcode primer, for example, using PCR techniques. The barcode primer is an identifier sequence that allows the sequence reads to be separated into the appropriate library. Thus, the barcode primer allows for demuliplexing after sequencing.

Then each of the amplified control promoter library, the amplified non-induced promoter library and the amplified induced promoter library are sequenced using quantitative next generation sequencing to provide a plurality of sequenced promoters. Each of the plurality of sequenced promoters can be found in one or more of the control promoter library, the non-induced promoter library and the induced promoter library.

In an aspect, sequencing comprises next generation sequencing (NGS), also called high throughput, massively parallel, or deep sequencing. While there are different platforms that allow for NGS, all NGS platforms provide for the parallel sequencing of millions of DNA sequences. Next generation sequencing allows for the quantitation of the proportion of a sequence in each gate, and for normalization across the total of sequence number.

For each promoter sequence, the fluorescence can be ascertained from the gate in which it was found. If the gate width is too narrow, a promoter sequence may be found in multiple gates because fluorescence follows a Gaussian distribution. In such a case, the effective fluorescence of that promoter sequence is measured as a weighted sum across multiple, where the weights represent normalized abundance within each gate.

The fluorescence change for different conditions can then be determined for each sequenced promoter under the different conditions, specifically, control with no DNA binding protein, non-induced and induced.

Metrics are then provided for the sequenced promoters. At least five metrics can be measured for each promoter sequence: fluorescence level of constitutive promoter, promoter repressed by DNA binding protein, and promoter induced by adding inducer, fold repression (ratio of fluorescence of constitutive promoter to promoter repressed by DNA binding protein), and fold induction or an association constant (ka) dynamic range (ratio of fluorescence of promoter+DNA binding protein+inducer to promoter+DNA binding protein). The method thus includes providing a control metric, a non-induced metric, and/or an induced metric for at least a portion of the plurality of sequenced promoters based upon identification of each of the at least a portion of the plurality of sequenced promoters in the control promoter library, the non-induced promoter library and/or the induced promoter library. The metric(s) can be obtained for each unique promoter sequence. Depending on the size of the promoter library, we can quantify the "phenotype" of thousands to hundreds of thousands of promoter sequences simultaneously. The control metric, non-induced metric, and/or induced metric are then used to determine the induction/repression for the at least a portion of the plurality of sequenced promoters.

From the control metric, the non-induced metric and the induced metric for each of the at least a portion of the plurality of sequenced promoters, an induction/repression property is then determined.

An induction table is then provided including each of the at least a portion of the plurality of sequenced promoters comprising the promoter sequence and the control metric, non-induced metric, and induced metric, wherein the control metric, non-induced metric, and induced metric provide an induction/repression property of the promoter sequence for the DNA binding protein and the inducer molecule.

Kinetic profiles can also be extracted. For example, a dose-response experiment, carrying out induction at different inducer concentrations, will allow us to measure additional performance characteristics such as operational range (ligand responsiveness upper and lower bound) and transfer function (through Hill coefficient curve fitting) of induction response.

Finally, based upon the induction table, a synthetic promoter having a specified induction and/or repression for the DNA binding protein and the inducer molecule is selected.

Further included herein are biosensors comprising a synthetic promoter identified by the process described herein, wherein the biosensor is responsive to the concentration of the inducer molecule. In an aspect, the synthetic promoter does not comprise the sequence bound by the DNA binding protein in nature.

The invention is further illustrated by the following non-limiting examples.

EXAMPLES

Example 1: Brief Description of the Method of Designing Synthetic Promoters

Step 1: In vitro Selection for Non-Native Promoters that Bind to an Allosteric Transcription Factor.

Figure 2:
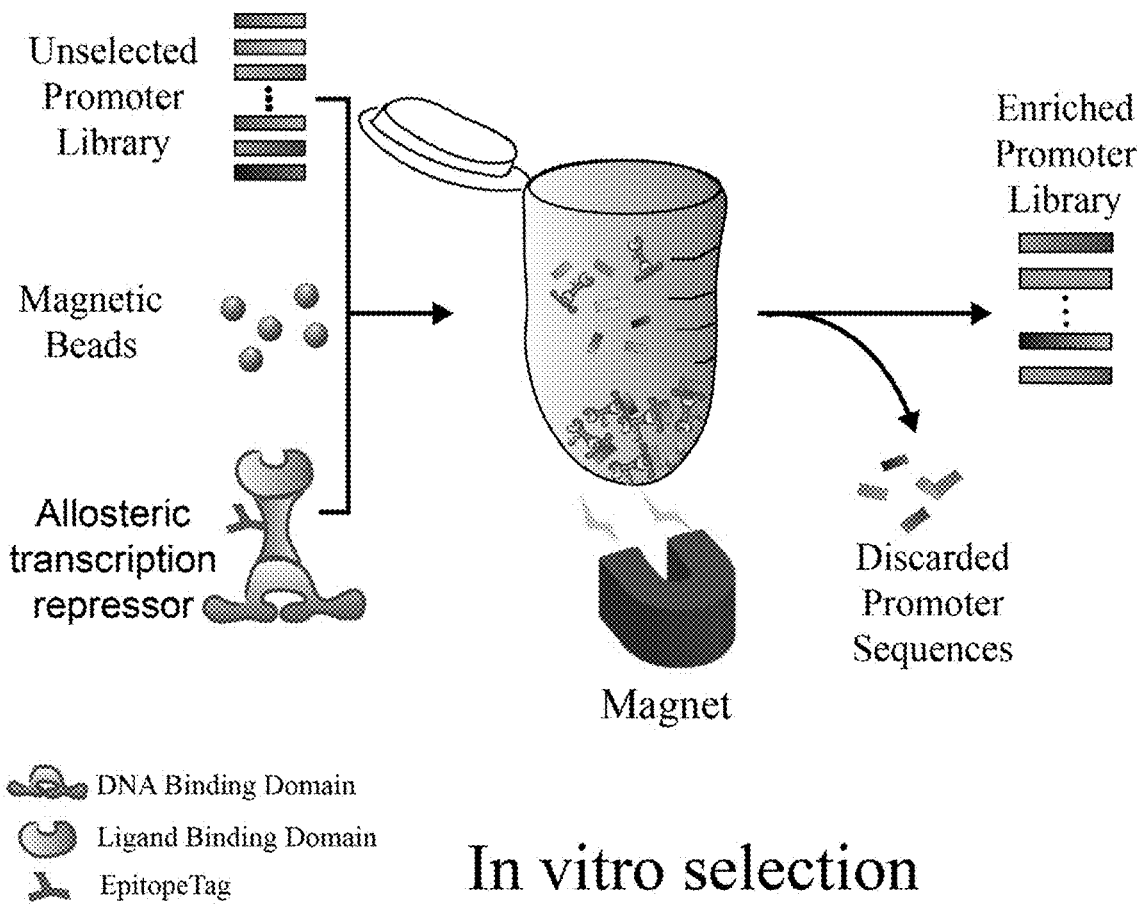
FIG. 2 is an embodiment of an in vitro selection protocol to provide an enriched library of promoters.

Starting from random sequences, a first population of DNA sequences that bind to an allosteric transcription factor (aTF) is selected to produce an enriched library of operator sites. An embodiment of the in vitro selection is provided in FIG. 2.

First, an unselected polynucleotide library is provided that includes a plurality of random degeneracies over one or more regions of a known constitutive promoter. Exemplary libraries are provided in Example 2. An exemplary unselected polynucleotide is 12 to 40 base pairs, specifically 16 to 19 base pairs in length. In an alternative aspect, the unselected polynucleotide library comprises any set of random degeneracies, for example, to identify operator sequences for an aTF of unknown specificity.

Second, the polynucleotide sequences that bind the allosteric transcription factor are selected from the unselected polynucleotide library to provide the enriched polynucleotide library. The enriched polynucleotide library is enriched for sequences that bind the allosteric transcription factor with a range of affinities that can be determined by the experimenter, for example, by varying the buffer conditions used for binding, such as salt concentration and pH. The enriched polynucleotide library thus includes a plurality of operator sequences that bind to the allosteric transcription factor with a range of affinities. The in vitro selection can be performed by any suitable method such as a pull-down method or an electrophoretic mobility shift assay (EMSA) method. In either method, the allosteric transcription factor, the unselected polynucleotide library, or both may comprise a label such as an affinity tag, a radioactive tag or a fluorescent tag.

Step 2: In vivo Selection of the Enriched Library

Figure 3:
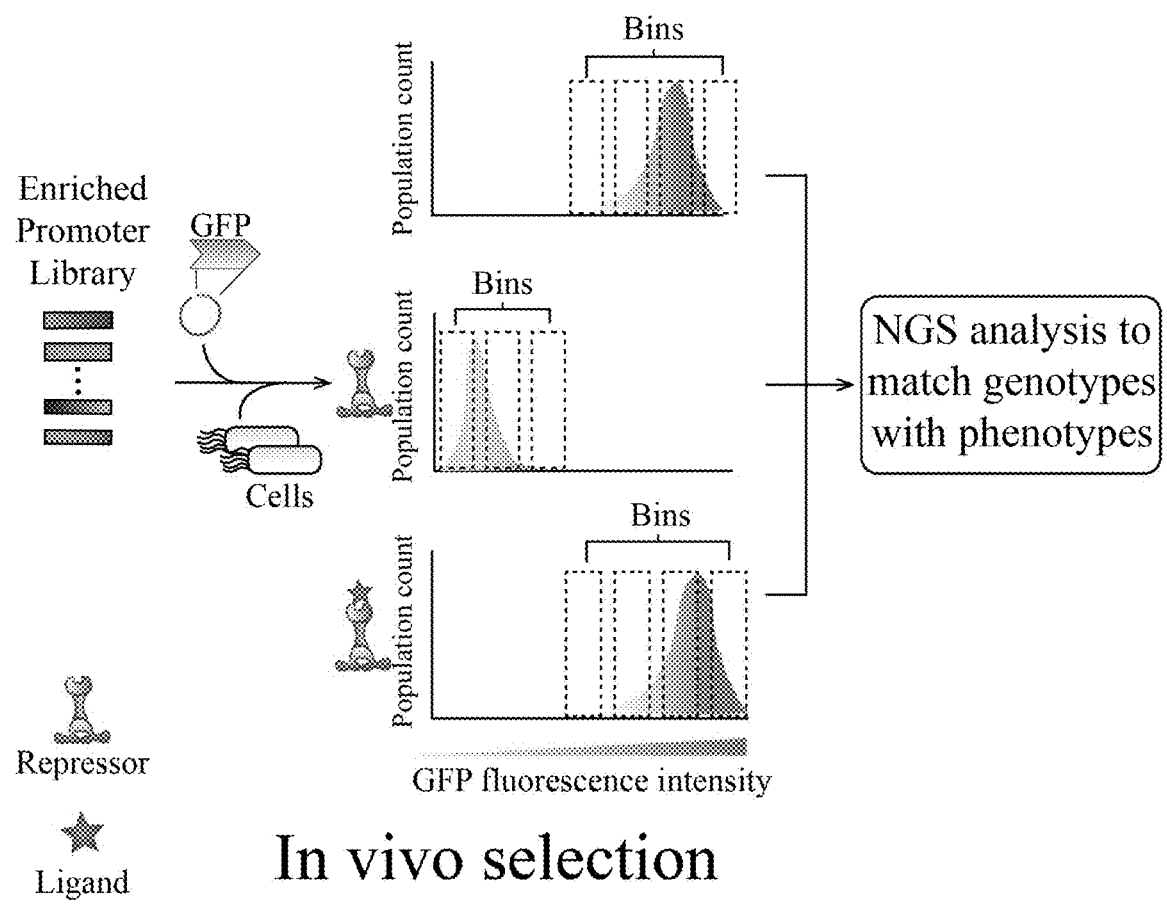
FIG. 3 is an embodiment of the in vivo selection.

Once the enriched polynucleotide library that is enriched for sequences that bind the allosteric transcription factor has been produced, the gene expression activity of the enriched polynucleotide library is measured in vivo to simultaneously compute the induction level of the members of the enriched polynucleotide library. This is carried out by binning and sequencing three populations: enriched polynucleotide library alone, enriched polynucleotide library+aTF, enriched polynucleotide+aTF+inducer. FIG. 3 shows an embodiment of the in vivo activity measurement.

In an aspect, the DNAs from the first enriched polynucleotide library are inserted into a constitutive promoter either between or flanking the RNA polymerase binding sites (e.g., containing the consensus −35 (TTGACA) and −10 sites (TATAAT) in the case of E. coli). This unit is operably linked to a ribosome binding site and a reporter gene (e.g., GFP), for example in an appropriate vector such as a plasmid, to produce a reporter vector, which is then transformed into a host strain such as E. coli. The host strain co-expresses the allosteric transcription factor used for the in vitro selection. The host strain is then grown to provide a culture. The culture is divided into two split cultures and an inducer molecule for the allosteric transcription factor is added into one of the split cultures to provide a non-induced culture and an induced culture. A control culture transformed with the plurality of reporter vectors with no allosteric transcription factor expression is also prepared. The control culture, the non-induced culture and the induced culture are sorted by reporter protein intensity (e.g., fluorescence intensity) to provide a sorted control culture, a sorted non-induced culture, and a sorted induced culture. Sorting can be done, for example, using FACS.

Binning of the sorted control culture, the sorted non-induced culture and the sorted induced culture produces one or more control gates, one or more non-induced gates and one or more induced gates. The gates provide a convenient means by which to group the control promoter sequences, non-induced promoter sequences and induced promoter sequences by activity level. A gate is a portion of a culture comprising a plurality of polynucletotides (e.g., promoters) of specified reporter intensities. The one or more control gates comprises a control promoter library, the one or more non-induced gates comprises a non-induced promoter library, and the one or more induced gates comprises the induced promoter library.

In a specific aspect, the activity of each promoter sequence is measured in terms of reporter GFP level. To simultaneously measure the activity of all the promoters, we classify them into bins based on GFP fluorescence. The number of bins is adjusted depending on the range of promoter activities exhibited. The width of each bin is limited by the accuracy of cell sorting. A "gate" is applied in the cell sorter to collect cells within a fluorescence range. The gates provide a convenient means by which to group the control sequences and induced sequences by activity level. A gate is a portion of a culture comprising a plurality of promoters of specified reporter intensities. Cells containing the enriched polynucleotide library, enriched polynucleotide library+aTF, enriched polynucleotide library+aTF+inducer are sorted based on their activity.

Step 3: Sequencing and Analyzing the Control Promoter Library, the Non-Induced Promoter Library and the Induced Promoter Library The control promoter library, the non-induced promoter library, and the induced promoter library are then sequenced and analyzed.

The control promoter library, the non-induced promoter library and the induced promoter library are cultured, for example, overnight, prior to sequencing. The control promoter library, the non-induced promoter library, and the induced promoter library are amplified, for example, using PCR, prior to sequencing. Amplification can be done with a sequencing primer and a barcode primer, for example.

In a specific example, cells from each bin are grown till they reach optical density (OD600) of 0.1-0.2. Their plasmids are harvested and promoter sequence is amplified by 10-15 cycles of PCR amplification. Each bin is assigned a unique barcode primer for demultiplexing after next-generation sequencing.

In an aspect, sequencing comprises next generation sequencing (NGS), also called high throughput, massively parallel, or deep sequencing. While there are different platforms that allow for NGS, all NGS platforms provide for the parallel sequencing of millions of DNA sequences. Next generation sequencing allows for the quantitation of the proportion of a sequence in each gate, and for normalization across the total of sequence number.

For each promoter sequence, the fluorescence can be ascertained from the bin in which it was found. If the bin width is too narrow, a promoter sequence may be found in multiple bins because fluorescence follows a Gaussian distribution. In such a case, the effective fluorescence of that promoter sequence is measured as a weighted sum across multiple, where the weights represent normalized abundance within each bin.

The fluorescence change for different conditions can then be determined for each sequenced promoter under the different conditions, specifically, control with no allosteric transcription factor, non-induced and induced.

At least five metrics can be measured for each promoter sequence: fluorescence level of constitutive promoter, promoter repressed by aTF, and promoter induced by adding inducer, fold repression (ratio of fluorescence of constitutive promoter to promoter repressed by aTF), and fold induction or an association constant (ka) dynamic range (ratio of fluorescence of promoter+aTF+inducer to promoter+aTF).

The metric(s) can be obtained for each unique promoter sequence. Depending on the size of the promoter library, we can quantify the "phenotype" of thousands to hundreds of thousands of promoter sequences simultaneously.

Thus, the quantitative NGS allows for providing a control metric, a non-induced metric, and/or an induced metric for at least a portion of the plurality of sequenced promoter based upon identification of the at least a portion of the plurality of sequenced promoters in the control promoter library, the non-induced promoter library and/or the induced promoter library. The control metric, non-induced metric, and/or induced metric are then used to determine the induction/repression for the at least a portion of the plurality of sequenced promoters.

The induction/repression properties of the at least a portion of the plurality of sequenced promoters can be expressed as a table of promoters that states the sequence of the promoter, metric (e.g., expression level as reported by fluorescence) under all three conditions (promoter, promoter+aTF, promoter+aTF+inducer), fold repression and fold induction (or dynamic range).

Kinetic profiles can also be extracted. For example, a dose-response experiment, carrying out induction at different inducer concentrations, will allow us to measure additional performance characteristics such as operational range (ligand responsiveness upper and lower bound) and transfer function (through Hill coefficient curve fitting) of induction response.

Using the induction table, a synthetic promoter having a specified induction and/or repression for the allosteric transcription factor and the inducer molecule is selected. In an aspect, the selected synthetic promoter may be used to prepare a vector comprising the synthetic promoter, e.g., operator operably linked to a ribosome binding site. The allosteric transcription factor may be expressed from the same vector, or may be expressed from a different vector.

Example 2: Exemplary Unselected Promoter Library

The following exemplary unselected promoter libraries are based on the TetR family transcription repressors. The library is designed to include the *E. coli* RNA polymerase holoenzyme interacting −35 and −10 regions. The library also includes a constant RBS site. Other accessory sequences are for the promoter architecture or cloning purposes. The library is illustrated in FIG. 4.

The components of the library sequences include:

```
Ribosome binding site:
                                          (SEQ ID NO: 1)
GAATTCATTAAAGAGGAGAAAGGT -35 site: TTGACA
```

-continued

-10 Site: TATAAT

BsaI recognition sequence: GGTCTC

BasI recognition cut site: CTGA

Control Sequence:
(SEQ ID NO: 2)
TGCGACGGTCTCACTGAGGCGCGCCTTGACATCGCATCTTTTTGTACCTA

TAATAGATTCATGATGAGAATTCATTAAAGAGGAGAAAGGT

Libraries:
CSI 16N-BsaI:
(SEQ ID NO: 3)
TGCGACGGTCTCACTGAGGCGCGCCTTGACANNNNNNNNNNNNNNNNTAT

AATAGATTCATGATGAGAATTCATTAAAGAGGAGAAAGGT

CSI 17N-BsaI:
(SEQ ID NO: 4)
TGCGACGGTCTCACTGAGGCGCGCCTTGACANNNNNNNNNNNNNNNNNTA

TAATAGATTCATGATGAGAATTCATTAAAGAGGAGAAAGGT

CSI 18N-BsaI:
(SEQ ID NO: 5)
TGCGACGGTCTCACTGAGGCGCGCCTTGACANNNNNNNNNNNNNNNNNNT

ATAATAGATTCATGATGAGAATTCATTAAAGAGGAGAAAGGT

CSI 19N-BsaI
(SEQ ID NO: 6)
TGCGACGGTCTCACTGAGGCGCGCCTTGACANNNNNNNNNNNNNNNNNNN

TATAATAGATTCATGATGAGAATTCATTAAAGAGGAGAAAGGT

Figure 5:
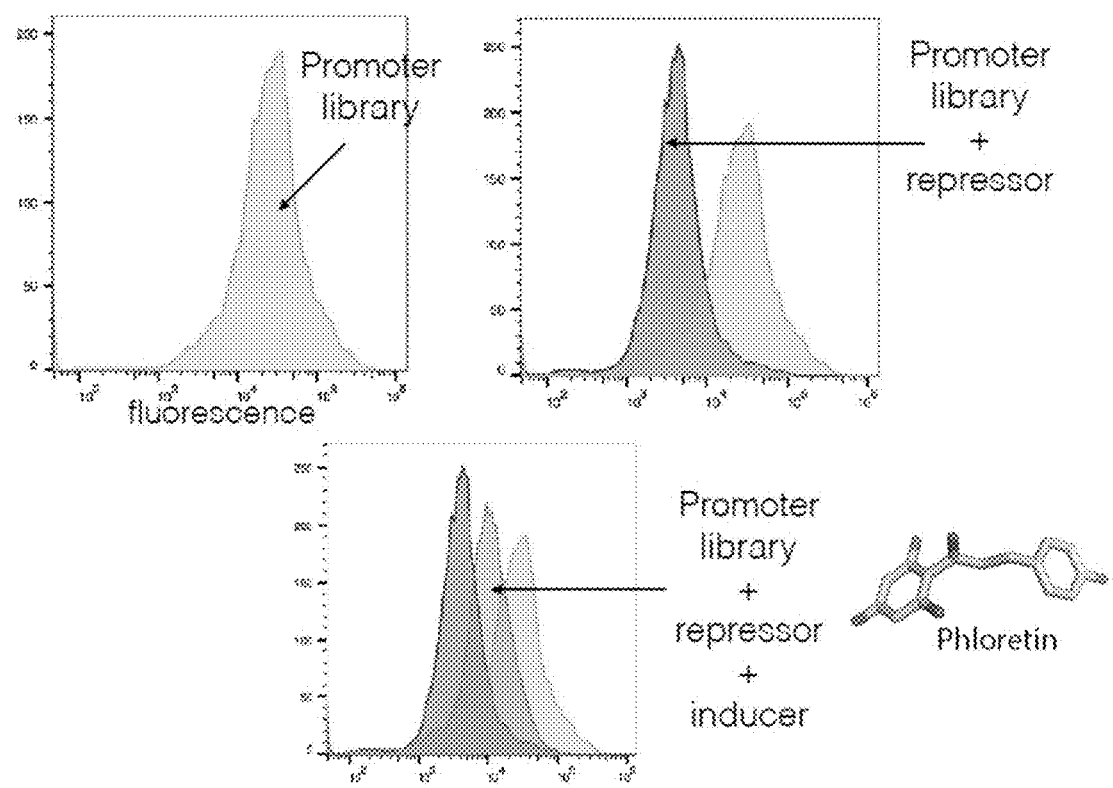
FIG. 5 shows the distributions for PmeR, a flavonoid-responsive allosteric transcription factor, produced by the methods described herein.

Example 3: Results for PmeR-a Flavonoid-Responsive Allosteric Transcription Factor In this example, the allosteric transcription factor was PmeR (repressor) and the inducer molecule was naringenin. The results are shown in FIG. 5.

The post in vitro enrichment of polynucleotides (with PmeR protein) was cloned into a vector to drive the expression of a green fluorescent protein using the Golden Gate assembly method. Following the transformation and over-night growth in E. coli DH10B, the fluorescent intensity distribution was profiled using a flow cytometer with 488 nm laser and 510 (25) nm filter. The delivery of the transcription repressor was through a second vector containing constitutively expressing PmeR protein. The fluorescent intensity distribution shift was captured with a flow cytometer after over-night growth. A decrease of overall fluorescent intensity was observed. The induction assay was conducted with the addition of 300 uM naringenin to the previous E. coli population with decreased fluorescence. Following the over-night growth, an overall increase in fluorescent intensity was captured with a flow cytometer measurement.

Figure 6:
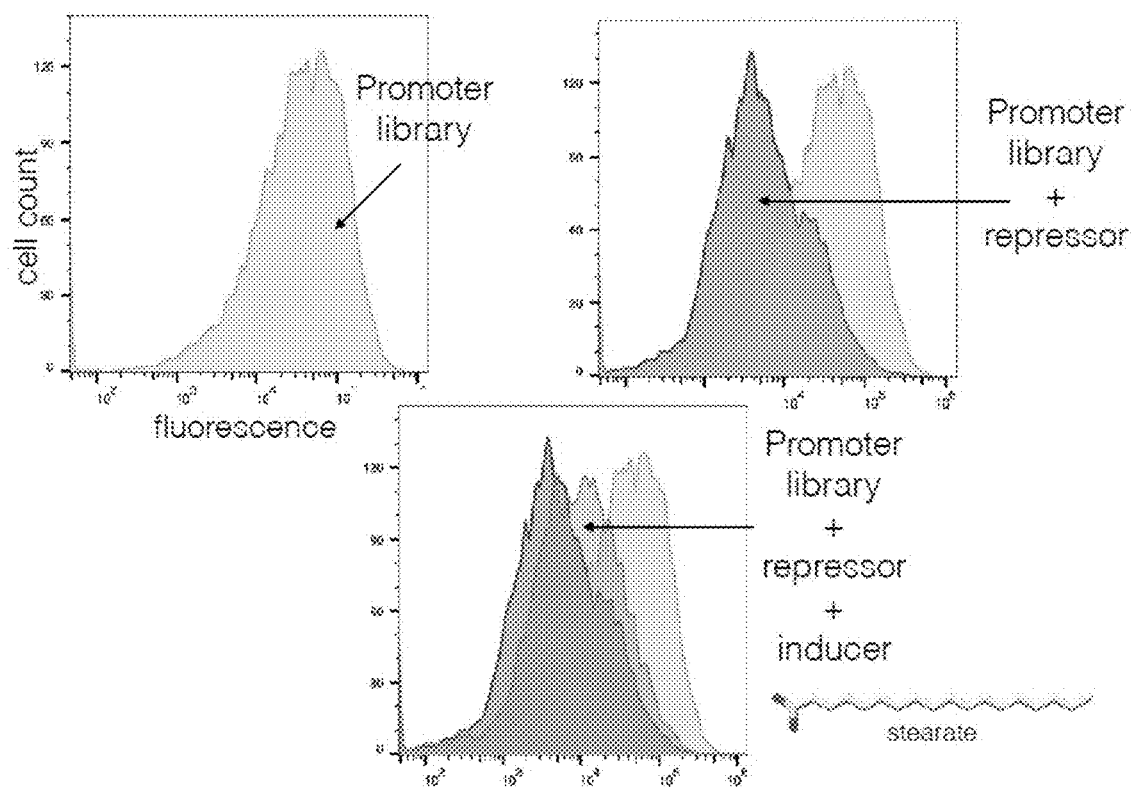
FIG. 6 shows the distributions for DesT, a stearate-responsive allosteric transcription factor, produced by the methods described herein.

Example 4: Results for DesT-a Stearate-Responsive Allosteric Transcription Factor In this example, the allosteric transcription factor was DesT (repressor) and the inducer molecule was stearate (sodium salt). The results are shown in FIG. 6.

The post in vitro enrichment of polynucleotides (with DesT protein) was cloned into a vector to drive the expression of a green fluorescent protein using the Golden Gate assembly method. Following the transformation and over-night growth in E. coli DH10B, the fluorescent intensity distribution was profiled using a flow cytometer with 488 nm laser and 510 (25) nm filter. The delivery of the transcription repressor was through a second vector containing constitutively expressing DesT protein. The fluorescent intensity distribution shift was captured with a flow cytometer after over-night growth. A decrease of overall fluorescent intensity was observed. The induction assay was conducted with the addition of 250 uM stearate to the previous E. coli population with decreased fluorescence. Following the over-night growth, an overall increase in fluorescent intensity was captured with a flow cytometer measurement.

For example, for bacterial repressor TtgR, results are given in Table 5:

TABLE 5

Promoter sequences and induction/repression

| Promoter sequence (including -35 and -10 regions) | Repressed (au) | Induced with 400 µM naringenin (au) | Fold induction | Induced with 400 µM phloretin (au) | Fold induction |
|---|---|---|---|---|---|
| TTGACATACATACGCGT GTGTATGTATAAT SEQ ID NO: 7 | 6512 | 20241 | 3.1 | 33643 | 5.2 |
| TTGACATACAATCACG GTTGTATATAAT SEQ ID NO: 8 | 26598 | 50162 | 1.9 | 77021 | 2.9 |
| TTGACATACATGCGTG AATGTATGTTATAAT SEQ ID NO: 9 | 5135 | 10300 | 2.0 | 16383 | 3.2 |
| TTGACATACATCCATGA GTGTATGTATAAT SEQ ID NO: 10 | 2939 | 18533 | 6.3 | 40363 | 13.7 | au - arbitrary fluorescence units

Example 5: Systematic Evolution and Characterization of Inducible Promoters for Each of the 6 TetR Family aTFs Besides the sequences provided in examples 3 and 4, we also systematically evolved and characterized thousands of inducible promoters for each of the 6 TetR family aTFs. The results are shown in FIG. 7.

Figure 7:
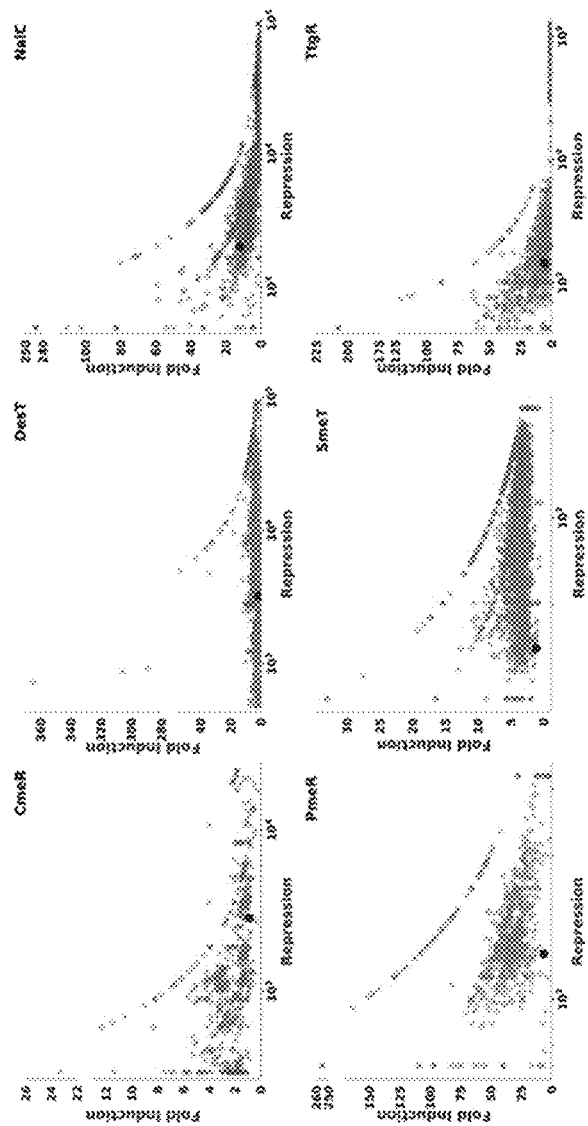
FIG. 7 shows the fold induction and repression (repressed state fluorescence) of thousands of inducible promoters generated using the method for 6 TetR family aTFs. The native promoters of 6 aTFs are indicated as a black dot in each panel of the figure.

In FIG. 7, each dot presents a promoter with unique fold induction and repression profiles. We also tested the native promoters for 6 TetR family aTFs by operably linking each native promoter to a RBS and a reporter protein (the same RBS and reporter protein used for the promoter libraries). Native promoters' fold induction and repression profiles are included in the figure and marked as a single black dot in each panel of the figure. Native promoters are the promoters repressed by aTFs in their native host organisms.

The fold induction results are also summarized Table 6. Sequences of native promoters are shown in Table 7.

TABLE 6

Fold induction results

| Transcription factor | Native promoter fold induction | Designed promoters' fold induction range | Presence of designed promoters (Yes/No) |
|---|---|---|---|
| PmeR | 6 | 1-50 | Yes |
|  |  | 50-100 | Yes |
|  |  | 100-200 | Yes |
|  |  | >200 | Yes |
| TtgR | 6 | 1-50 | Yes |
|  |  | 50-100 | Yes |
|  |  | 100-200 | Yes |
|  |  | >200 | Yes |
| NalC | 12 | 1-50 | Yes |
|  |  | 50-100 | Yes |
|  |  | 100-200 | Yes |
|  |  | >200 | Yes |
| CmeR | 1 | 1-10 | Yes |
|  |  | 10-20 | Yes |
|  |  | 20-30 | Yes |
|  |  | 30-40 | No |
| SmeT | 1 | 1-10 | Yes |
|  |  | 10-20 | Yes |
|  |  | 20-30 | Yes |
|  |  | 30-40 | Yes |
| DesT | 1 | 1-50 | Yes |
|  |  | 50-100 | Yes |
|  |  | 100-200 | No |
|  |  | >200 | Yes |

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

TABLE 7

Transcription factors and native promoter sequences

| Transcription factor | SEQ ID NO: | Native promoter sequence |
|---|---|---|
| PmeR | 11 | gTTTACAAACAACCGCGAATGTAAGTATATTCCTTAGCA |
| TtgR | 12 | TATTTACAAACAACCATGAATGTAAGTATATTCCTTAGCA |
| NalC | 13 | TTGACGCTGGTCATTTAAGAACTGTATCGTACAGTACT |
| CmeR | 14 | TTTCTGTAATAAATATTACAATTTTTAATTTAATTTTTC |
| SmeT | 15 | TTTACAAACAACAAGCATGTATGTATATTTCGCACCCATCA |
| DesT | 16 | AGTGAACGCTTGTTGACTCGATTGCGCGGAACGGGCAAAGTTTTGTGAACGATCGTTCAC |

The invention claimed is:

1. A method of identifying a synthetic inducible promoter, comprising in vitro selecting a first population of polynucleotides that bind to a DNA binding protein to produce an enriched polynucleotide library by providing an unselected polynucleotide library comprising a plurality of random degeneracies over one or more regions of a 12 to 40 base pair polynucleotide sequence, and selecting from the unselected polynucleotide library a plurality of polynucleotide sequences that bind the DNA binding protein to provide the enriched polynucleotide library;

in vivo selecting from the enriched polynucleotide library a second population of polynucleotides that repress or induce production of a reporter protein to produce an induced promoter library by operably linking the enriched polynucleotide library to a ribosome binding site and a reporter gene to provide a plurality of reporter vectors, transforming the plurality of reporter vectors into a host strain which co-expresses the DNA binding protein, and growing the host strain provide a culture, and dividing the culture into two split cultures and adding an inducer molecule for the DNA binding protein into one of the two split cultures to provide a non-induced culture and an induced culture, and sorting a control culture transformed with the plurality of reporter vectors with no DNA binding protein expression, the non-induced culture, and the induced culture by reporter protein intensity, to provide a sorted control culture, a sorted non-induced culture, and a sorted induced culture, and binning the sorted control culture, the sorted non-induced culture and the sorted induced culture to produce one or more control gates, one or more non-induced gates and one or more induced gates, wherein the one or more control gates comprises a control promoter library, the one or more non-induced gates comprises a non-induced promoter library, and the one or more induced gates comprises the induced promoter library, wherein a gate is a culture portion comprising a plurality of promoters of specified reporter intensities;

sequencing and analyzing the control promoter library, the non-induced promoter library and the induced promoter library by culturing and then amplifying the control promoter library, the non-induced promoter library and the induced promoter library, to provide an amplified control promoter library, an amplified non-induced promoter library and an amplified induced promoter library, quantitatively next generation sequencing the amplified control promoter library, the amplified non-induced promoter library, and the amplified induced promoter library to provide a plurality of sequenced promoters, providing a control metric, a non-induced metric, and/or an induced metric for at least a portion of the plurality of sequenced promoters based upon identification of each of the at least a portion of the plurality of sequenced promoters in the control promoter library, the non-induced promoter library and/or the induced promoter library, determining, from the control metric, the non-induced metric and the induced metric for each of the at least a portion of the plurality of sequenced promoters an induction/repression property, and providing an induction table including each of the at least a portion of the plurality of sequenced promoters comprising the promoter sequence and the control metric, non-induced metric, and induced metric, wherein the control metric, non-induced metric, and induced metric provide an induction/repression property of the promoter sequence for the DNA binding protein and the inducer molecule; and selecting, based upon the induction table, a synthetic promoter having a specified induction and/or repression for the DNA binding protein and the inducer molecule.

2. The method of claim 1, wherein the DNA binding protein is an allosteric transcription factor, an allosteric activator, a signaling protein, or a eukaryotic nuclear receptor.

3. The method of claim 2, wherein the allosteric activator comprises LysR, AtzR, IlvY, MetR, MdcR, CysB, AraC, XylS, RhaR, UreR, LuxR, AhyR, QscR, HapR, Lrp, AsnC, LrpA, LrpC, Crp, FnR, Vfr, IclR, RexZ, SsfR, MerR, BltR, BmrR, Mta, CueR, ZntR, PbrR, or DhaS.

4. The method of claim 1, wherein selecting from the unselected promoter library a plurality of promoter sequences that bind the DNA binding protein to provide the first enriched promoter library comprises a pull-down method using an affinity tagged DNA binding protein, an electrophoretic mobility shift assay using an radioactive or fluorescent labeled unselected promoter library, or a protein-binding microarray.

5. The method of claim 1, wherein the reporter is GFP or FbFP.

6. The method of claim 1, wherein the DNA binding protein is an allosteric transcription factor that is from an LTTR family, an AraC/XylS family, a DeoR family, a DtxR family, a Fur family, a GntR family, an LuxR family, an Lrp/AsnC family, a Crp/Fnr family, an IclR family, a MerR family, a MarR family, a LacI/GalR, a TetR family, a transcription factor associated with amino acid metabolism, a prokaryotic two-component transcription factor, or a eukaryotic nuclear receptor transcription factor.

7. The method of claim 1, wherein the DNA binding protein is an allosteric transcription factor that is CmeR, CymR, DesT, LmeA, NalC, PmeR, QacR, RolR, SmeT, TetR, or TtgR.

8. The method of claim 1, wherein the enriched polynucleotide library is downstream of a −10 site, upstream of a −35 site, or overlaps these sites in the reporter vectors.

9. The method of claim 1, wherein the enriched polynucleotide library is operably linked to a transcription regulatory site.

10. The method of claim 9, wherein the transcription regulatory site is a TATA box.

11. The method of claim 1, wherein multiple polynucleotide libraries are operably linked to the ribosome binding site and the reporter gene.

12. The method of claim 1, wherein the inducer is a sugar molecule, a metallic ion, an antimicrobial agent, a dye, a flavonoid, or a combination comprising at least one of the foregoing.

13. The method of claim 1, wherein the inducer is lactose, IPTG, L-arabinose, maltose, trehalose, glucose-6P, glycerol-P, glucitol, fucose, L-ascorbate, deoxyribonucleoside, inositol, fructose, Hg(II), Cu(II), Ag(I), Au(I), Zn(II), Pb(II), Cd(II), anhydrotetracyclin, chloramphenicol, resorcinol, proflavine, rifamycin, actinorhodin, simocyclinone D8, triclosan, ethidium, rhodamine6G, tetraphenylphosponim, quercetin, fisetin, galangin, phlorotin, naringenin, cetachin, coumestrol, stearate, Oleate, c-d-AMP, cholate, salicylate, a glucocorticoid, or an estrogen mineralocorticoid.

14. The method of claim 1, wherein the gate comprising a plurality of promoters of specified reporter intensities is selected by florescent-activated-cell-sorting.

15. The method of claim 1, wherein the host strain comprises organisms of the genus *Escherichia, Bacillus, Staphylococcus, Caulohacter, Streptococcus, Thermus, Streptomyces, Mycoplasma, Aliivibrio, Synechocystis, Azotobacter, Pseudomonas, Agrobacterium, Zymomonas, Saccharomyces, Yarrowia, Pichia*, or a combination comprising at least one of the foregoing.

16. A biosensor comprising a synthetic promoter identified by the process of claim 1, wherein the biosensor is responsive to the concentration of the inducer molecule.

17. The biosensor of claim 16, wherein the synthetic promoter does not comprise the sequence bound by the DNA binding protein in nature.

* * * * *